(12) United States Patent
Napolitano

(10) Patent No.: US 7,872,007 B2
(45) Date of Patent: Jan. 18, 2011

(54) PROCESS FOR THE PREPARATION OF 2-(4-HYDROXY-3-MORFOLYNIL)-2-CYCLOHEXENONE

(75) Inventor: Elio Napolitano, Pisa (IT)

(73) Assignee: Abiogen Pharma S.p.A., Pisa (IT)

( * ) Notice: Subject to any disclaimer, the term of this patent is extended or adjusted under 35 U.S.C. 154(b) by 134 days.

(21) Appl. No.: 12/279,323

(22) PCT Filed: Feb. 12, 2007

(86) PCT No.: PCT/IT2007/000088
§ 371 (c)(1),
(2), (4) Date: Aug. 13, 2008

(87) PCT Pub. No.: WO2007/094022
PCT Pub. Date: Aug. 23, 2007

(65) Prior Publication Data
US 2009/0030199 A1    Jan. 29, 2009

(30) Foreign Application Priority Data
Feb. 13, 2006 (IT) .......................... MI2006A0258

(51) Int. Cl.
*A61K 31/5375* (2006.01)
*C07D 265/30* (2006.01)
(52) U.S. Cl. .................................. 514/238.8; 544/173
(58) Field of Classification Search ........................ None
See application file for complete search history.

(56) References Cited

FOREIGN PATENT DOCUMENTS

| DE | 10 04 191 B | 3/1957 |
|---|---|---|
| EP | 0 314 147 A2 | 5/1989 |
| EP | 1 518 536 A2 | 3/2005 |
| WO | WO 2004/111021 A1 | 12/2004 |

OTHER PUBLICATIONS

Brown, J.S. 1971 "Oxidation of reduced nicotinamide nucleotides by diamide (*NNN'N'*-Tetramethylazoformamide)" *Biochem. J.*, 124: 665-667.

*Primary Examiner*—Yong Chu
*Assistant Examiner*—Michael Barker
(74) *Attorney, Agent, or Firm*—Knobbe Martens Olson & Bear LLP

(57) ABSTRACT

It is disclosed a process for the preparation of 2-(4-hydroxy-3-morfolinyl)-2-cycloesenone (BTG-1675A) comprising the steps of: i) reacting N-hydroxymorpholine with cycloesanone in the presence of an oxidation agent thus obtaining an isoxazolidine of Formula IV; and ii) converting the isoxazolidine of Formula IV into 2-(4-hydroxy-3-morfolinyl)-2-cycloesenone. Advantageously, the oxidation agent of the step i) is selected from the group consisting of metal oxides, esters and amides of the azodicarboxylic acid and the step ii) of conversion is carried out by basic catalysis followed by trituration in an aromatic hydrocarbon, preferably toluene. The process disclosed allows to obtain BTG-1675A according to the invention in an amount of hundreds of grams and on an industrial scale. The invention further concerns a new process for preparing hydroxylamines, particularly N-hydroxymorpholine, which is used in the process for preparing BTG-1675A.

20 Claims, No Drawings

PROCESS FOR THE PREPARATION OF 2-(4-HYDROXY-3-MORFOLYNIL)-2-CYCLOHEXENONE

This application is U.S. National Phase of International Application PCT/IT2007/000088, filed Feb. 12, 2007 designating the U.S., and published in English as WO 2007/094022 on Aug. 23, 2007, which claims priority to Italian Patent Application No. MI2006A000258, filed Feb. 13, 2006.

The present invention concerns a process for the preparation of 2-(4-hydroxy-3-morfolinyl)-2-cyclohexenone starting from N-hydroxymorpholine. The invention concerns also a new process for the preparation of hydroxylamines, particularly N-hydroxymorpholine.

The compound 2-(4-hydroxy-3-morfolinyl)-2-cyclohexenone of Formula I

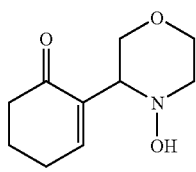

Formula I also known as BTG-1675A, is a substance which has been recently described in the International application n. PCT/GB2004/002324 (Publication n. WO2004/111021) as medicament for the treatment of depression and anxiety, particularly for the treatment of anxiogenesis caused by withdrawal from benzodiazepines, or caused by abruptly ceasing the administration of substances such as nicotine, alcohol and cocaine.

According to the International document, BTG-1675A is obtained by a process which provides for the reaction between a nitrone, i.e. a compound of Formula II

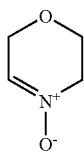

Formula II and cyclohexenone of Formula III

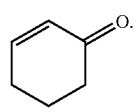

Formula III

Specifically, in the International document, BTG-1675A is obtained by a process which provides for the following steps:
a) oxidising morpholine in order to produce the compound of Formula II, through a reaction of a catalysed oxidation;
b) adding cyclohexenone; and
c) isolating and purifying BTG-1675A through distillation and chromatography.

As described in the example 1 of the cited international application, the step a) of reaction occurs at a reaction temperature of 0° C. for about an hour and half, by using an excess of hydrogen peroxide as oxidant and sodium tungstate as catalyst. In the same reaction vessel cyclohexenone (of Formula III) of step b) is then added and the cyclohexenone reacts with the nitrone of Formula II, which is formed in situ after the step a), for further 48 hours in a temperature range from the ambient temperature to 100° C. Subsequently the reaction mixture is heated at a temperature of about 55° C. for two hours and then at 65° C. for further 2 hours. As indicated in the document, the formation of a intermediate of Formula IV (cycloaddition compound),

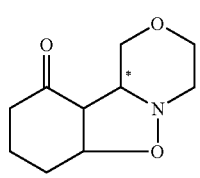

Formula IV is obtained, from which the compound of the invention is obtained in situ either by protonation or by basic catalysed reaction.

Although such a process is very simple in its realization, it shows the drawback of producing only few grams of BTG-1675A with a yield of only about 14%, which makes it unsuitable for the application on industrial scale. Furthermore, such a yield of 14% is obtained owing to a complicated chromatographic purification process which produces a considerable amount of waste products.

In order to increase the yield many attempts were made by trying to make amendments of the reaction condition or by applying recent methods of conversion of morpholine to nitrone, i.e. the compound of Formula II. All such attempts turned out to be vain, because from the analysis of the reaction mixture an incomplete oxidation of morpholine, scarce conversion of the compound of Formula IV, presence of high amount of N-hydroxymorpholine, spread decomposition of the reaction crude material in the distillation were revealed, by obtaining substantially scarce production of the compound of interest (Forcato, M.; Nugent, W. A.; Licini, G. *Tetrahedron Lett.* 2003, 44, 49; Murray, R. W.; Iyanar, K. *J. Org. Chem.* 1996, 61, 8099; Goti, A.; Nannelli, L. *Tetrahedron Lett.* 1996, 37, 6025).

It is still felt the need of a process which allows to obtain BTG-1675A in an amount of hundred grams and which is therefore suitable to such a production on industrial scale.

Therefore, an object of the present invention is to obtain a high amount of BTG-1675A through a process which is convenient for the production on industrial scale.

It is a further object of the invention to obtain the compound BTG-1675A in high yield and purity so as to be used as medicament.

Such objects have been achieved by a process for the preparation of 2-(4-hydroxy-3-morpholinyl)-2-cyclohexenone of Formula I

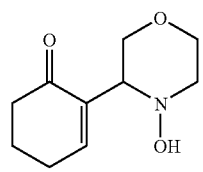

Formula I comprising the steps of:
i) reacting N-hydroxymorpholine of Formula V

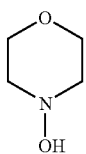

Formula V with cyclohexenone of Formula III

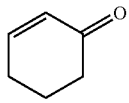

Formula III in the presence of an oxidation agent thus obtaining an isoxazolidine of Formula IV

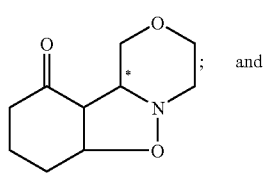

Formula IV

; and ii) converting isoxazolidine of Formula IV into 2-(4-hydroxy-3-morpholinyl)-2-cyclohexenone.

According to the invention, step i) occurs in the presence of a wide variety of bland oxidation agents, preferably the metallic oxides such as mercury oxide, lead dioxide, activated manganese dioxide and silver oxide.

In particular, mercury oxide allows an effective oxidation of N-hydroxymorpholine according to the invention. However, its transformation during the oxidation into metallic mercury is deemed slightly advantageous on a wide scale process because of the high toxicity of the metallic mercury. Activated manganese dioxide gives less problems for its toxicity, but requires a difficult management of the manganese dioxides which are produced by the reaction and whose elimination through the filtration from the apparatuses is hard.

In the attempt of searching alternative solutions, the inventors of the present invention have surprisingly found out that ester and amide derivatives of the azodicarboxylic acid are optimal oxidation agents which allow the oxidation of N-hydroxymorpholine in the presence of cyclohexenone reaching yields which are comparable to the ones obtainable by mercury oxide or activated manganese dioxide without having their drawbacks. Among the ester derivatives, diethylazodicarboxylate, diisopropylazodicarboxylate, diethylazodicarboxylate supported on a polymeric material, di-tert-buthylazodicarboxylate, dibenzylazodicarboxylate can be cited. Among the amide derivatives of the azodicarboxylic acid, azodicarboxamide, 1,1'-(azodicarbonyl)dipiperidine and the cyclic derivative 1-phenyl-1,2,4-triazoline-2,5-dione can be cited.

In still another aspect of the invention, the invention pertains the use of the ester and amide derivatives of the azodicarboxylic acid as oxidation agents. In particular, ester and amide derivatives of azodicarboxylic acid can be used for the oxidation of hydroxylamine. In the present description the term "hydroxylamine" is intended as a secondary amine having alicyclic or cyclic chain and which is N-hydroxy substituted. More preferably, such derivatives are used for the oxidation of N-hydroxymorpholine.

Preferably, the oxidation agent of the process according to the invention is azodicarboxamide. Such a substance is known in industry as anti-foaming agent in polymers and as additive in bread. The cost of azocarboxamide is low, particularly if compared to mercury oxide and activated manganese dioxide, which, besides having a higher prize on the market, are generally used in great excess. Advantageously, azodicarboxamide, used in step i) of the process according to the invention, turns into idrazodicarboxamide, which is a practically insoluble solid in the reaction mixture and therefore can be easily removed by filtration. More advantageously, the so obtained idrazodicarboxamide can be retransformed into azodicarboxamide, through an oxidation reaction with e.g. hydrogen peroxide or electrochemically. Therefore the process according to the invention, when the oxidation agent is azodicarboxamide, can provide a step of recycling the oxidation agent by means of transformation of idrazodicarboxamide into azodicarboxamide.

The reaction between N-hydroxymorpholine and cyclohexenone in the presence of the oxidation agent of step i) occurs preferably in less than one hour and at a temperature from 40 to 100° C., still more preferably at about 70° C. The reaction of step i), apart from the oxidation agent, allows yields of the product of Formula IV higher than at least 50% and when the oxidation agent is selected from the group consisting of mercury oxide, activated manganese oxide and azodicarboxamide the yield will be preferably about 75%.

N-hydroxymorpholine is a known compound which is accessible through different routes (O'Neil, I. A.; Cleator, E. T *Tetrahedron Lett.* 2001, 42, 8247; Rogers M. A. T. *J Chem. Soc.* 1955, 769). It is surprisingly found that it is possible to obtain N-hydroxymorpholine by a synthetic route which is alternative to the known ones, thus obtaining it with yield and purity levels suitable to the aim according to the process and in a more convenient way. In another aspect therefore the invention concerns a process to obtain hydroxylamines, which comprises the step of reacting a secondary amine with an oxidation agent in excess, in the presence of catalytic amount of a ketone which is particularly electrophilic. The term "particularly electrophilic ketone" is intended as a ketonic organic compound capable to accept electrons such as e.g. trihydrate hexafluoro acetone, ninidrine; preferably it is trihydrate hexafluoro acetone. Preferably according to the invention such a process allows to obtain N-hydroxymorpholine. The product N-hydroxymorpholine is so obtained by starting from morpholine, with yield of 95% and purity of 85%.

Advantageously, N-hydroxymorpholine can be further purified by precipitating the salt which it forms with p-toluensolphonic acid. N-hydroxymorpholine is so obtained by decomposition with sodium carbonate in acetone. The yield according to this process is of about 60% with respect to the initial morpholine.

In order to obtain N-hydroxymorpholine, the oxidation agent is preferably hydrogen peroxide or hydrogen peroxide-urea complex. Still more preferably such a oxidation agent is hydrogen peroxide in excess.

Preferably the oxidation reaction of morpholine to N-hydroxymorpholine occurs at a temperature from 20 to 80° C., still more preferably at about 50° C.

N-hydroxymorpholine obtained according to the invention, either raw or purified, is preferably used as a starting reagent to obtain BTG-1675A according to the invention. According to such a process by means of the reaction with cyclohexenone in the presence of oxidation agent, N-hydroxymorpholine turns into isoxazolidine of Formula IV, which is converted into BTG-1675A in the subsequent step ii). Such a conversion reaction is advantageously promoted either thermally or by basic catalysis.

In case of basic catalysis, when a bland basic catalyst is used, e.g. triethylamine in methanol or stoichiometric amount of NaOH in methanol, BTG-1675A is slowly formed thus producing a mixture in equilibrium in which the compound of Formula IV and BTG-1675A are in a ratio of 2:3. Advantageously the use of an excess of sodium metoxide in order to shift the equilibrium to BTG-1675A can be used.

In the present invention from the reaction promoted by the basic catalysis, preferably through triethylamine in hot methanol, advantageously BTG-1675A can be obtained as a pure compound with yield of 45% through trituration in an aromatic hydrocarbon, wherein isoxazolidine of Formula IV is considerably more soluble. From the evaporation of mother waters of the trituration, pure BTG-1675A can advantageously be obtained. In such a way, according to the present invention, by taking into account the recovery material which has not been converted, it is hence possible to obtain a transformation of isoxazolidine into BTG-1675A with yield of about 90%. Preferably the aromatic hydrocarbon for the trituration is toluene or benzene, still more preferably toluene.

The conversion of isoxazolidine of Formula IV into the compound BTG-1675A and the subsequent trituration in an aromatic hydrocarbon are, in the process according to the invention, advantageous and useful solutions to obtain BTG-1675A on an industrial scale.

Examples of preparation of N-hydroxymorpholine and BTG-1675A, which are given for exemplificative and non-limitative purposes, now follow.

EXAMPLE 1

Preparation of N-hydroxymorpholine

To a solution containing morpholine (174 mL, 2 mol) and hexafluoroacetone trihydrate (3 mL, 21 mmol) in acetone (350 mL), kept under mechanical stirring in a three necked round bottom flask (surmounted by a reflux condenser), $H_2O_2$ (200 mL of a solution 30%, 3.6 mol) was added dropwise. The addition was followed by a progressive increasing of temperature and, after the addition of about 50 mL, the solution started to vigorously reflux; the addition was adjusted so as to keep a constant reflux. When the addition was over, the solution was left to stir for one hour and then evaporated under reduced pressure by a rotavapor, while the temperature of the bath was kept at 50° C. The reddish yellow residue of the evaporation was suspended in ethylacetate (500 mL) and the mixture saturated with sodium chloride; the organic phase of the solution (the upper layer) was then separated and the aqueous phase extracted twice with ethyldiacetate (250 mL). The collected organic extracts were dried on anhydrous sodium carbonate (20 g) and evaporated at reduced pressure by rotavapor, while the temperature of the bath was kept to 50° C. Raw N-hydroxymorpholine was then obtained (190 g, 92%, yield 85% purity, the remaining being mainly constituted by unreacted morpholine). Raw N-hydroxymorpholine was then used for the preparation of BTG-1675A.

A sample (1 g, 10 mmol) of the raw obtained N-hydroxymorpholine was purified through the following method:

The sample was dissolved in acetone (10 mL); in the solution so obtained and heated, p-toluenesulphonic acid was dissolved (1.9 g, 10 mmol); from the mixture brought to 4° C., p-toluenesulphonate of N-hydroxymorfolinium (1.9 g, 65%) was separated as a white crystalline solid: m.p. 152-154° C.

$^1$H-NMR (DMDO-d6) 2.27 (3H, s), 1.54 (2H, m) 3.54-3.69 (4H, m), 3.97 (2H, m), 7.14 (2H, d, J=8 Hz), 7.51 (2H, d, J=8 Hz). $^{13}$C-NMR (CDCl$_3$): 20.9, 55.5, 62.6, 125.6, 128.5, 138.6, 144.6. The salt so obtained was added to a suspension of anhydrous sodium carbonate (1 g, 10 mmol) in acetone (20 mL) and the mixture was magnetically stirred for 12 hours; the solid was then removed by filtration and from the evaporation of the filtrate, purified N-hydroxymorpholine (0.65 g, 100%) was obtained as colourless oil. 1H-NMR (CDCl3) 2.54 (2H, t, J=11 Hz), 3.04 (2H, d, J=11 Hz) 3.49, (2H, t, J=11 Hz), 3.80 (2H, d, J=11 Hz), 7.9 (1H, bs). 13C-NMR (CDCl3): 58.9, 66.6.

EXAMPLE 2

Preparation of 2-(4-hydroxy-3-morfolinyl)-2-cyclohexenone (BTG-1675A)

Step i) Reaction of N-hydroxymorpholine with Cyclohexenone and Production of Isoxazolidine of Formula IV A mixture containing raw N-hydroxymorpholine obtained by Example 1 (190 g), 2-cyclohexenone (120 mL, 1.25 mol) and azodicarboxamide (235 g, 2 mol) in ethylacetate (500 mL), which was kept under mechanical stirring in a round bottom flask surmounted by a reflux condenser, was cautiously heated until the reaction became exothermic, thus allowing the mixture to spontaneously reflux; at the end of the spontaneous heating, the mixture was heated to reflux for 4 hours. In this time, the bright yellow solid of azodicarboxamide turned into a whitish solid. The still warm content of the round bottom flask was then transferred in a glass column provided with a porous septum and the solution was filtered by applying pressure; the solid in the column was washed with hot ethylacetate (400 mL). The collected filtrates were evaporated under reduced pressure to give a semisolid residue to which methanol was added (200 mL); the mixture was firstly heated in order to triturate the semisolid mass and solubilize the oily fraction, then let it to cool at −20° C.; isoxazolidine of Formula IV (130 g, 54% with respect to cyclohexenone) was collected as colourless crystalline solid; m.p. 101-102° C. $^{13}$C-NMR (CDCl$_3$) 17.8, 28.1, 39.2, 50.4, 53.2, 64.6, 65.6, 66.1, 76.0, 210.9.

Step ii) Conversion of Isoxazolidine of Formula IV into the Compound BTG-1675A

A mixture consisting of isoxazolidine of Formula IV obtained as above in step i) (500 g, 2.5 mol), triethylamine (100 mL) and methanol (1 L) was heated to reflux for 24 hours and thus evaporated under reduced pressure. The residue was suspended in toluene (1.3 L) and a portion of solvent was evaporated under reduced pressure in a rotavapor (bath temperature: 70° C.) until the distillate was clear; the volume of the mixture was brought to about 800 mL, by adding toluene and the mixture was cooled in a bath of water and ice. The precipitate was collected by filtration under vacuum and washed once with cold toluene to give a mixture of isoxazolidine of Formula IV and BTG-1675A as a colourless crystalline mass (490 g, 98%). The mass was suspended in toluene (1 L) preheated at 70° C. and the mixture was kept under vigorous stirring while it was left to re-equilibrate with the room temperature; the solid, collected by filtration under vacuum, was subjected still twice to the above described cycle of trituration in hot toluene followed by cooling and filtering; thus pure BTG-1675A (230 g, 46%, 90% based on the amount of collected mixture of isoxazolidine and BTG-1675A; purity higher than 98%) was obtained as a crystalline solid of ice-white colour; m.p. 127-128° C. $^1$H-NMR (CDCl$_3$) 1.96 (2H, m), 2.41 (4H, m), 2.83 (1H, dt, J=3.5 and 11.5 Hz), 3.06 (1H, t, J=11.5 Hz), 3.20 (1H, d, J=11 Hz), 3.54-3.90 (4H, m), 5.45 (1H, bs), 7.12 (1H, t, 4.3 Hz). $^{13}$C-NMR (CDCl$_3$): 23.2, 26.5, 38.9, 58.9, 64.5, 67.2, 71.9, 136.2, 148.8, 199.1. The collected filtrates coming from triturations were evaporated to give a residue from which a mixing consisting of isoxazolidine and BTG-1675A in the ratio of 5:1 (245 g, 49%) was obtained by trituration in cold ethylether.

As the above example shows, the process according to the invention allows to obtain 2-(4-hydroxy-3-morpholinyl)-2-cyclohexenone in an amount of hundreds of grams and with high yields, which makes the process according to the invention suitable for producing BTG-1675A on an industrial scale.

Furthermore BTG-1675A obtained by the process according to the invention can be advantageously purified and used as a medicament.

The invention was described with reference to two examples of preparation, but modifications, such as the use of a different oxidation agent, can be provided without going beyond the scope of protection of the appended claims.

What is claimed is:

1. A process for the preparation of 2-(4-hydroxy-3-morpholinyl)-2-cyclohexenone of Formula I

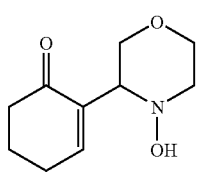

Formula I comprising the steps of:
i) reacting N-hydroxymorpholine of Formula V

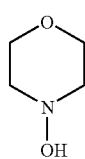

Formula V with cyclohexenone of Formula II

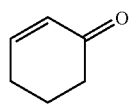

Formula III in the presence of an oxidation agent thus obtaining an isoxazolidine of Formula IV

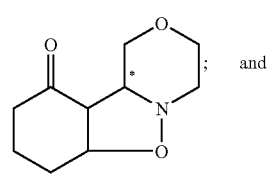

Formula IV and ii) converting isoxazolidine of Formula IV into 2-(4-hydroxy-3-morpholinyl)-2-cyclohexenone.

2. The process according to claim 1 wherein the oxidation agent is selected from the group consisting of metal oxides, esters and amides of azodicarboxylic acid.

3. The process according to claim 2 wherein the oxidation agent is selected from the group consisting of mercury oxide, lead dioxide, activated manganese dioxide, silver oxide, diethylazodicarboxylate, diisopropylazodicarboxylate and azodicarboxamide.

4. The process according to claim 3 wherein the oxidation agent is mercury oxide or activated manganese dioxide.

5. The process according to claim 3 wherein the oxidation agent is azodicarboxamide.

6. The process according to claim 5 further comprising a step of recycling of the oxidation agent azodicarboxamide through separation of the reaction product hydrazodicarboxamide obtained by step i) and its conversion into azodicarboxamide.

7. The process according to claim 1, wherein the step i) occurs in less than one hour and at a temperature from 40 to 100° C., preferably at about 70° C.

8. The process according to claim 1, wherein the yield of isoxazolidine of Formula IV is higher than at least 50%.

9. The process according to claim 1, wherein the yield of isoxazolidine is about 75%.

10. The process according to claim 1, wherein the conversion of step ii) is carried out thermally or by basic catalysis.

11. The process according to claim 10, wherein the conversion is carried out by basic catalysis by means of a basic catalyst selected from triethylamine in methanol and NaOH in methanol.

12. The process according to claim 10, wherein 2-(4-hydroxy-3-morpholinyl)-2-cyclohexenone is obtained pure by trituration in an aromatic hydrocarbon.

13. The process according to claim 12, wherein the aromatic hydrocarbon is toluene or benzene.

14. The process according to claim 13 wherein the aromatic hydrocarbon is toluene.

15. The process according to claim 14 wherein 2-(4-hydroxy-3-morpholinyl)-2-cyclohexenone is obtained with yield of about 45%.

16. The process according to claim 1, wherein N-hydroxymorpholine of step i) is N-hydroxymorpholine obtained by a process comprising a step of reacting morphiline with an oxidation agent in excess, in the presence of catalytic amounts of a particularly electrophilic ketone.

17. The process according to claim 16, wherein the oxidation agent is hydrogen peroxide in excess or a hydrogen peroxide-urea complex.

18. The process according to claim 16 wherein the oxidation agent is hydrogen peroxide in excess.

19. The process according to claim 16, wherein the particularly electrophilic ketone is trihydrate hexafluoro-acetone or ninidrine.

20. The process according to claim 16, wherein the particularly electrophilic ketone is hexafluoro-acetone trihydrate.

* * * * *